US007226939B2

(12) United States Patent
Chandavarkar et al.

(10) Patent No.: US 7,226,939 B2
(45) Date of Patent: Jun. 5, 2007

(54) THIENOPYRIDINE ANALOGUES WITH ANTIFUNGAL ACTIVITY AND PROCESS THEREOF

(76) Inventors: Mohan A. Chandavarkar, 7B Chand Terrace, St. Andrews Road, Bandra (IN) 400 500; Vithal Madhavrao Kulkarni, Dept. of Chemical Techology (UDCT), Univeristy of Mumbai, Nathalal Parikh Marg, Matunga, Mumbai (IN) 400 019; Pranavkumar Shivkumar, House No. 536, Raghunath Peth, Angol, Belgaum (IN) 590 007; Ravindra S. Shetty, FDC Limited 142-148, S.V. Road, Jogeshwari (West), Mumbai (IN) 400 102; Uday Rojaram Bapat, FDC Limited 142-148, S.V. Road, Jogeshwari (West), Mumbai (IN) 400 102

( * ) Notice: Subject to any disclaimer, the term of this patent is extended or adjusted under 35 U.S.C. 154(b) by 306 days.

(21) Appl. No.: 10/503,313

(22) PCT Filed: Feb. 11, 2003

(86) PCT No.: PCT/IN03/00024

§ 371 (c)(1),
(2), (4) Date: Aug. 2, 2004

(87) PCT Pub. No.: WO03/068142

PCT Pub. Date: Aug. 21, 2003

(65) Prior Publication Data

US 2005/0020653 A1 Jan. 27, 2005

(30) Foreign Application Priority Data

Feb. 12, 2002 (IN) ......................... 125/02

(51) Int. Cl.
*A61K 31/41* (2006.01)
*A61K 31/415* (2006.01)
*C07D 249/08* (2006.01)
*C07D 233/00* (2006.01)

(52) U.S. Cl. .................. 514/383; 514/385; 548/262.2; 548/266.2; 548/300.1

(58) Field of Classification Search ................ 514/383, 514/385; 548/262.2, 266.2, 300.1
See application file for complete search history.

(56) References Cited

U.S. PATENT DOCUMENTS 4,529,799 A * 7/1985 Richardson et al. ........ 546/256
6,653,330 B2 * 11/2003 Uchida et al. .............. 514/340

FOREIGN PATENT DOCUMENTS

EP 0046337 * 7/1981

* cited by examiner

*Primary Examiner*—Joseph K. McKane
*Assistant Examiner*—Susannah L. Chung
(74) *Attorney, Agent, or Firm*—David A. Guerra

(57) ABSTRACT

The invention relates to novel antifungal compounds and its pharmaceutically acceptable salts, having as part of its structure, imidazolyl or benzimidazolyl derivatives. The imidazolyl derivative may be substituted at 2 position from among the group consisting of aroyl, p-chloroaroyl, phenyl hydroxy methine or p-chloro phenyl hydroxy methine or with n-butyl at 2 position and chlorine at 4 and 5 position. In the alternative, when it is a benzimadazolyl derivative, with hydrogen at 6 position, the substituent at 2 position may be selected from among methyl, ethyl, isopropyl, 2-oxo-propl-1-yl, n-propyl, methoxy methyl, propen-1-yl, phenyl, p-chlorophenyl, p-toluyl, benzyl, 4-pyridyl, p-methoxy phenyl, 3-pyridyl, o-methoxy phenyl, styryl, 2-cyano methyl, p-hydroxy phenyl, p-amino phenyl, p-toluyl sulfonyl methyl or p-(t-butyl) phenyl group and if hydrogen is at 2 position, the substituent at the 6 position is selected from among nitro, trifluoromethyl or methoxy group.

10 Claims, No Drawings

THIENOPYRIDINE ANALOGUES WITH ANTIFUNGAL ACTIVITY AND PROCESS THEREOF

FIELD OF INVENTION

The invention relates to a novel compound which are triazole derivatives useful in the treatment of fungal infections in animals, including humans and as agricultural fungicides.

BACKGROUND OF INVENTION

In the past two decades the frequency and types of life-threatening fungal infections have increased dramatically in immuno-compromised patients. Several factors have contributed to this rise such as the expansion of severely ill and or immuno-compromised patient populations with HIV infection, with chemotherapy induced neutropenia, and receiving immunosuppressive therapy; more invasive medical procedures, such as extensive surgery and the use of prosthetic devices and vascular catheters; treatment with broad-spectrum antibiotics or glucocorticosteroids; and peritoneal dialysis or hemodialysis.

This problem of increased fungal infections is accentuated by the emergence of fungal strains which are resistant to currently used antifungal agents. Major opportunistic fungal pathogens include *Candida albicans, Aspergillus, Fusurian* spp. Other species of *Candida* such as *C. krusei, C. tropicalis, C. glabrata* are major causative agents of candidiasis. Invasive pulmonary aspergillosis is a leading cause of mortality in bone marrow transplant recipients. HIV-infected patients are particularly susceptible to mucosal candidiasis, cryptcoccal meningitis.

Fluconazol is the preferred broad spectrum anti-fungal agent used in treatment of fungal infections. In recent times resistance of *Candida albicans* the most common cause of mucosal candidiasis in HIV-infected patients, after long-term suppressive therapy, to azoles, particularly fluconazole, is a cause of increasing concern. Resistance to fluconazole in other *Candida* species and in *Cryptococcus neoformans* has also been reported. Also, fluconazole appears to be less active against the two emerging *Candida* species, *C. glabratta* and *C. krusei*. Infection with *Aspergillus*, although not common, is frequently life-threatening, and fluconazole has only moderate activity against this fungi.

This has necessitated the need for new antifungal agents with broad spectrum of antifungal activity, which this invention seeks to provide.

SUMMARY

In its main aspect, the invention consists of a compound of formula (I), and its pharmaceutically acceptable salts

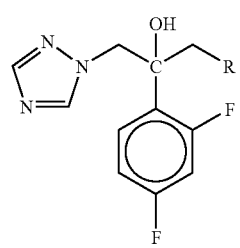

(I)

wherein R is imidazolyl derivative (II) or benzimidazolyl derivative (III).

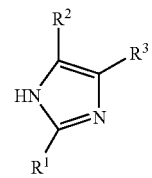

(II)

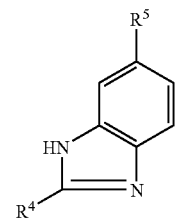

(III)

When R is Imidazolyl (II), $R^2$ and $R^3$ are hydrogen and $R^1$ is selected from among aroyl, p-chloroaroyl, phenyl hydroxy methine or p-chloro phenyl hydroxy methine, and when $R^1$ is n-butyl, $R^2$ and $R^3$ are chlorine. In the alternative, when R is a benzimadazolyl (III), $R^5$ is hydrogen and $R^4$ is selected from among methyl, ethyl, isopropyl, 2-oxoprop-1-yl, n-propyl, methoxy methyl, propen-1-yl, phenyl, p-chlorophenyl, p-toluyl, benzyl, 4-pyridyl, p-methoxy phenyl, 3-pyridyl, o-methoxy phenyl, styryl, 2-cyano methyl, p-hyrdroxy phenyl, p-amino phenyl, p-toluyl sulfonyl methyl or p-(t-butyl) phenyl group. In a further aspect, in benzimadazole (III) $R^4$ is hydrogen and $R^5$ can be selected from among nitro, trifluoromethyl or methoxy group.

In another aspect of this invention, the compound of Formula 1 is used along with pharmaceutically acceptable excipients.

In yet another aspect of the invention, the compound of Formula 1 is along with agriculturally acceptable diluants.

In the final aspect, the invention relates to a process whereby an oxirane (IV) is reacted with a imidazolyl derivative (II) or a benzimidazolyl derivative (III) as described above, in a solvent and in the presence of a base at elevated temperatures over a period of time, resulting in the synthesis of a compound which is an anti-fungal agent with broad spectrum activity.

DESCRIPTION

The main embodiment of the invention is given by the following description. Novel compounds of the formula (I) according to the invention can be obtained by the reaction of the oxirane of the formula (IV) or its methane sulphonate salt

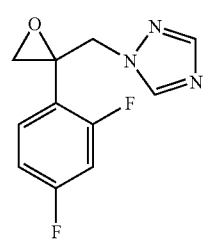

(IV)

with substituted imidazoles (II)

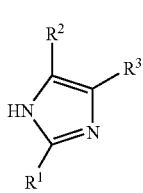
(II)

Where, $R^1$ is selected from among aroyl, p-chloroaroyl, phenyl hydroxy methine or p-chloro phenyl hydroxy methine and $R^2$ and $R^3$ are hydrogen or where $R^1$ is n-butyl and $R^2$ and $R^3$ are chlorine or with substituted benzimidazoles (III)

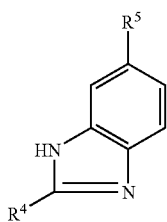
(III)

where $R^4$ is selected from among methyl, ethyl, isopropyl, 2-oxoprop-1-yl, n-propyl, methoxy methyl, propen-1-yl, phenyl, p-chlorophenyl, p-toluyl, benzyl, 4-pyridyl, p-methoxy phenyl, 3-pyridyl, o-methoxy phenyl, styryl, 2-cyano methyl, p-hyrdroxy phenyl, p-amino phenyl, p-toluyl sulfonyl methyl or p-(t-butyl) phenyl group and $R^5$ is hydrogen or where $R^4$ is hydrogen and $R^5$ is selected from among nitro, trifluoromethyl or methoxy group The reaction is carried out in the presence of a base, whereby the epoxide is opened to form the compound of formula (1).

The base used is selected from among sodium hydride, potassium carbonate, sodium hydroxide, potassium hydroxide, sodium carbonate, sodium methoxide, potassium t-butoxide. The reaction is carried out in a solvent selected from dimethyl sulfoxide, dimethyl formamide, tetrahydrofuran, dichloromethane, toluene, acetone or mixtures thereof. The choice of base and solvent used is not limited by the cited examples and the person skilled in art can select any other base in combination with any other solvent to get the desired results.

In a typical procedure oxirane (IV) or its methane sulphonate salt and substituted imidazole (II) or benzimidazole (III) are reacted together in a suitable solvent eg. dry dimethyl formamide preferably with heating from 60-140° C. for 8-24 hours. The progress of the reaction is monitored by Thin Layered Chromatography (TLC). The product is isolated and purified by conventional procedures.

The pharmaceutically acceptable salts of free bases which are acid addition salts is obtained by conventional procedures such as, mixing solutions containing equimolar amounts of free base and the desired acid together, followed by filtration to collect the required salt, if insoluble; or else by evaporation of the solvent from the system in accordance with the standard techniques.

The oxirane (IV) or its methane sulphonate salt can be obtained by conventional methods, typically from the corresponding acetophenone derivative (V) by

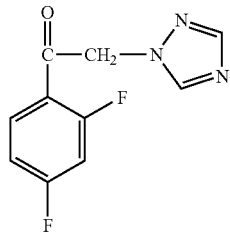
(V)

reacting it with sulfur ylide viz. dimethyl oxo sulfonium methylide prepared from trimethyl oxosulfonium iodide and a base. The methane sulphonate salt of IV can be obtained by treating IV in toluene or acetone with methane sulphonic acid.

The ketone (V) required for preparing the oxirane is synthesized by conventional methods.

For the purpose of the preferred embodiment of this invention, the oxirane (IV) may be prepared by the following method:

Preparation of 2-[(1H-1,2,4-triazol-1-yl)methyl]-2-(2,4-difluorophenyl)oxirane (IV)

An ylide is prepared from 2.19 gm (0.0099 mole) of trimethyloxosulfonium iodide, 0.43 gm (0.0099 mole, 55%) of sodium hydride, and 5 ml of dimethyl sulfoxide. To this, a solution of 2 gm (0.00896 mole) of acetophenone derivative (VII) in 5 ml of dimethyl sulfoxide is added. The reaction mixture is heated to 60° C. for 3 hours and poured over crushed ice after cooling. The product is isolated by extracting with ethyl acetate followed by repeated washings with saturated brine solution. The evaporation of solvent under reduced pressure gives titled compound as a dark brown oil (1.26 gm, 63%).

For the purpose of the preferred embodiment of this invention, the imidazoles (II) may be synthesized as per conventional methods as follows:

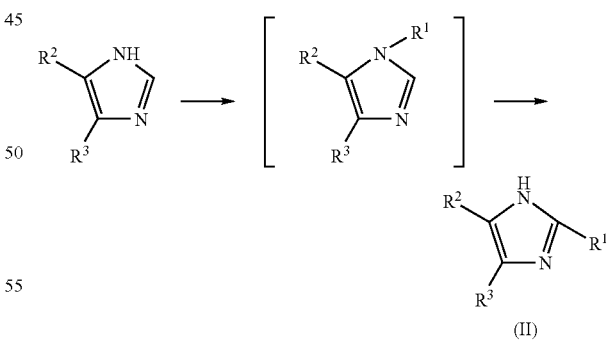

where, $R^1$, $R^2$ and $R^3$ are as defined earlier.

In a typical procedure 0.20 mole of aroyl chloride is added dropwise to a solution of 0.10 mole of imidazole and 0.20 mole of triethyl amine in 30 ml. of pyridine at 0°-10° C. under nitrogen atmosphere. The mixture is stirred for 3 hours at room temperature and then treated with aqueous sodium hydroxide. It is then heated to reflux for 1 hour, addition of 100 ml. of water and cooling lead to the precipitation of the product. The product is isolated by filtration and washed successively with water, ice-cold methanol and diethyl ether.

The corresponding alcohols are prepared by reducing ketones with sodium borohydride.

For the purpose of the preferred embodiment of this invention the benzimidazoles (III) may be synthesized as follows:

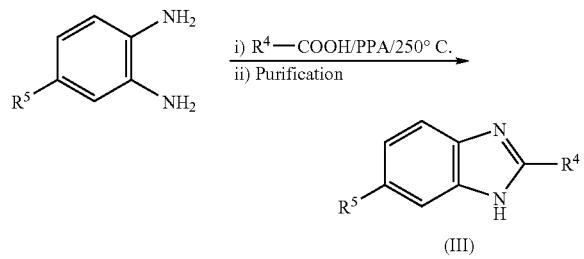

where, $R^4$ and $R^5$ are as defined earlier.

In a typical procedure equimolar amounts of o-phenylenediamine suitably substituted and the carboxylic acid (or its corresponding ester) are mixed with sufficient quantity of polyphosphoric acid (PPA) to give a stirrable paste. The mixture is slowly heated to 250° C., and the resulting solution is digested at 250° C. (±3° C.) for 4 hours, cooled to about 100° C. and poured in a thin stream into a large volume of rapidly stirred water. The insoluble residue is collected by filtration, washed with water and 10% sodium carbonate solution followed by water to remove residual alkalinity. The crude product is purified by recrystallization from alcohol or aq. alcohol mixture subsequent to treatment with a small amount of activated carbon or by column chromatography over silica gel (60-120) column.

THE FOLLOWING EXAMPLES DESCRIBE THE PREFERRED EMBODIMENT OF THIS INVENTION FOR PREPARATION OF COMPOUND OF FORMULA (I)

Example 1

Preparation of 1-(1H-1,2,4-triazol-1-yl)-2-(2',4'-difluorophenyl)-3-[2-(p-chloroaroyl)imidazol-1-yl]propan-2-ol 1H-[2-(p-chloro)aroyl]imidazole (1.169 g, 0.00566 mol) and oxirane (IV) (1.2 gm, 0.00506 mol), potassium carbonate (0.938 gm, 0.0068 mol) and dry dimethyl formamide (25 ml.) are stirred and heated together at 90° C. under nitrogen atmosphere. The progress of the reaction is monitored by TLC. After completion of reaction, reaction mixture is quenched in water and extracted with dichloromethane. Evaporation of solvent gives the titled compound (1.75 gm, 78%), melting point (193° C.-195° C.). The IR and NMR spectra of the compound are consistent with the structure.

Example 2

Preparation of 1-(1H-1,2,4-triazol-1-yl)-2-(2',4'-difluorophenyl)-3-(2-methyl-benzimidazol-1-yl)-propan-2-ol 1H-(2-methyl)-benzimidazole (0.748 gm, 0.00566 mol), oxirane (IV) (1.2 gm, 0.00506 mol), potassium carbonate (0.938 gm, 0.0068 mol) and dry dimethyl formamide (25 ml.) are stirred and heated together at 90° C. under nitrogen atmosphere. The progress of the reaction is monitored by TLC. After completion of reaction, reaction mixture is quenched in water and extracted with dichloromethane. Evaporation of solvent gives the titled compound (1.53 gm, 82%), melting point (207° C.-210° C.). The IR and NMR spectra of the compound are consistent with the structure.

Following the procedure as substantially described by above examples the various azole compounds of Formula (I) as mentioned herein are prepared.

The compound of Formula (I) and their pharmaceutically acceptable salts are antifungal agents effective to a greater or lesser extent, and useful in treating fungal infections in animals and humans, especially those caused by *C. albicans, Aspergillus* and *Fusarium*.

In vitro evaluation of antifungal activity can be performed by determining the minimum inhibitory concentration.

Anti-fungal susceptibility testing of these anti-fungal compounds was done by conventional method using soyabean casein digest broth. Known anti-fungal agents like Fluconazole and amphotericin-B were used as positive Control. End points were determined after 48 hours visually and by using Spectrophotometer wherever necessary. Different dilutions were tried and the set of experiments where repeated to confirm the end points. Standard cultures of *Candida, Aspergillus* and *Fusarium* were used for screening of these drugs.

Substituents and In-Vitro Anti-Fungal Activity (*C. albicans*) of the Compounds Expressed as MIC* (μg/ml). Reference Standard (RS) Fluconazole.

TABLE I

Compounds (I) formed from Imidazolyl derivatives (II)

| No | $R^1$ substitution | MIC μg/ml |
|---|---|---|
| 1. | Aroyl | <3.125 |
| 2. | p-chloro aroyl | <3.125 |
| 3. | Phenyl hydroxy methine | 25–50 |
| 4. | p-chlorophenyl hydroxy methine | 25–50 |

TABLE II

Compounds (I) formed from benzimidazolyl derivatives (III)

| No: | $R^4$ substitution | $R^{51}$ | MIC μg/ml |
|---|---|---|---|
| 1. | methyl | Hydrogen | 6.25–12.50 |
| 2. | Ethyl | Hydrogen | 6.25–12.50 |
| 3. | isopropyl | Hydrogen | 6.25–12.50 |
| 4. | 2-oxoprop-1-yl | Hydrogen | 6.25–12.50 |
| 5. | n-propyl | hydrogen | 25–50 |
| 6. | methoxymethyl | Hydrogen | 25–50 |
| 7. | Propen-1-yl | Hydrogen | 25–50 |
| 8. | phenyl | Hydrogen | 6.25–12.50 |
| 9. | p-chloro phenyl | Hydrogen | 6.25–12.50 |
| 10. | p-toluyl | Hydrogen | 100–200 |
| 11. | -Benzyl | Hydrogen | 100–200 |
| 12. | -4-pyridyl | Hydrogen | 100–200 |
| 13. | p-methoxy phenyl | Hydrogen | 50–100 |
| 14. | 3-pyridyl | Hydrogen | 100–200 |
| 15. | o-methoxy phenyl | Hydrogen | 50–100 |
| 16. | styryl | Hydrogen | 3.125–6.25 |
| 17. | Hydrogen | Nitro | 100–200 |
| 18. | Hydrogen | trifluoromethyl | 50–100 |
| 19. | Hydrogen | methoxy | 100–200 |

*Minimum Inhibitory Concentration (MIC) measured in terms of μg/ml

The activity of these compounds were tested against the reference standard of Fluconazole which showed minimum inhibitory concentration at <3.125 μg/ml.

Antifungal activity of these compounds also extends to *Aspergillus* and *Fusarium*. The activity seen in compound of Formula (1) as against these strains suggests that it exhibits broad spectrum antifungal activity For human use, the antifungal agents of formula (I) or a pharmaceutically acceptable salt may be administered alone, but is generally administered in an admixture with a pharmaceutically acceptable carrier, which is selected depending on the intended route of administration and standard medical practice. Thus it can be administered orally in the form of tablets, capsules or ovules or they can be injected intradermally, intramuscularly or subcutaneously.

For parenteral administration the compound is in the form of aqueous solution, along with other excipients. Alternatively, the antifungal compound of formula (I). can be administered in the form of supository or can be applied topically in the form of lotion, gel solution, cream, ointment or dusting powder.

We claim:

1. A compound of the formula

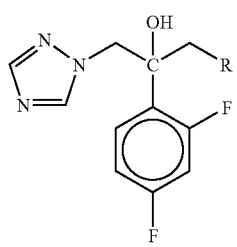

(I)

and its acceptable salt, where R is imidazolyl

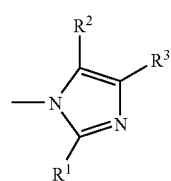

(II)

and R1 is p-chlorobenzoyl and R2 and R3 are hydrogen.

2. The compound as described in claim 1, where in the compound further comprising an excipient selected from the group consisting of a tablet, capsule, supository, ovule, lotion, gel solution, cream, ointment, and dusting powder.

3. A method of preparing a compound of the formula

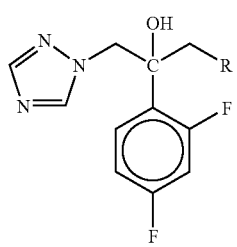

(I)

and its acceptable salt, where R is imidazolyl

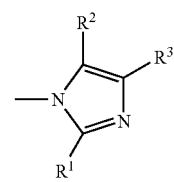

(II)

and wherein R1 is p-chlorobenzoyl and R2 and R3 are hydrogen, said method comprising the steps of:

reacting 2-[(1H-1,2,4-triazol-1-yl)methyl]-2-(2,4-diflurophenyl)oxirane (IV) or its methane sulphonate salt with substituted imidazole (II) in a solvent in the presence of a base at a temperature of 60° C. to 140° C. for a period of 8-24 hours;

isolating said compound by quenching said reaction mixture with water; and extracting said compound into an organic solvent.

4. The method as described in claim 3, wherein said oxirane (IV) is prepared by the steps comprising of:

preparing a ylide from trimethyloxosulfonium iodide, sodium hydride, and dimethyl sulfoxide;

adding to said ylide a solution of acetophenone derivative (VII) in dimethyl sulfoxide to form a mixture;

heating said mixture to a temperature about 60° C. for about 3 hours;

pouring said mixture over crushed ice after said mixture has cooled;

isolating said mixture by extracting with ethyl acetate; and washing said isolated mixture with saturated brine solution to produce a solvent;

evaporating said solvent under reduced pressure.

5. The method as described in claim 4, wherein said step of evaporating said solvent is performed until the compound is a dark brown oil.

6. The method as described in claim 3, wherein said base is selected from the group consisting of sodium hydride, potassium carbonate, sodium hydroxide, potassium hydroxide, sodium carbonate, sodium methoxide, and potassium t-butoxide.

7. The method as described in claim 4, wherein said solvent is selected from the group consisting of dimethyl sulfoxide, dimethyl formamide, tetrahydrofuran, dichloromethane, toluene, and acetone, or mixtures thereof.

8. The method as described in claim 7, wherein said base is potassium carbonate, and said solvent is dimethyl formamide.

9. The method as described in claim 8, wherein said oxirane (IV) imidazole (II), said potassium carbonate, and said dimethyl formamide are stirred and heated together at about 90° C. under nitrogen atmosphere to form a mixture.

10. The method as described in claim 9, wherein said mixture is extracted with dichloromethane.

* * * * *